US006537434B1

(12) United States Patent
McGrath et al.

(10) Patent No.: US 6,537,434 B1
(45) Date of Patent: Mar. 25, 2003

(54) FIRST DIMENSION ELECTROPHORESIS SEPARATION METHOD AND APPARATUS

(75) Inventors: Andrew McGrath, Burtonsville, MD (US); Jack Goodman, Lusby, MD (US); N. Leigh Anderson, Washington, DC (US)

(73) Assignee: Large Scale Proteomics Corporation, Germantown, MD (US)

( * ) Notice: Subject to any disclaimer, the term of this patent is extended or adjusted under 35 U.S.C. 154(b) by 252 days.

(21) Appl. No.: 09/621,484

(22) Filed: Jul. 21, 2000

(51) Int. Cl.[7] .................. G01N 27/26; G01N 27/447; G01N 35/00; G01N 35/10
(52) U.S. Cl. .................. 204/459; 204/456; 204/465; 204/606; 204/610; 204/615; 422/63; 422/64; 422/67; 436/43
(58) Field of Search .................. 204/456, 459, 204/465, 606, 610, 615; 422/63, 64, 65, 67; 436/43

(56) References Cited

U.S. PATENT DOCUMENTS

| | | | |
|---|---|---|---|
| 3,664,939 A | 5/1972 | Luner et al. | 204/548 |
| 3,915,839 A | 10/1975 | Rilbe et al. | 204/644 |
| 3,951,777 A | 4/1976 | Denckla | 204/644 |
| 4,048,049 A | * 9/1977 | Hoefer | 204/606 |
| 4,088,561 A | 5/1978 | Anderson | 204/610 |
| 4,217,193 A | 8/1980 | Rilbe | 204/451 |
| 4,284,491 A | * 8/1981 | Vesterberg | 204/606 |
| 4,495,279 A | 1/1985 | Karpetsky et al. | 435/6 |
| 4,670,119 A | 6/1987 | Hurd | 204/548 |
| 4,673,483 A | 6/1987 | Mandle | 204/627 |
| 4,747,919 A | 5/1988 | Anderson | 204/455 |
| 4,810,348 A | 3/1989 | Sarrine et al. | 204/608 |
| 4,827,780 A | 5/1989 | Sarrine et al. | 73/864.21 |
| 4,897,169 A | 1/1990 | Bier et al. | 204/548 |
| 4,963,236 A | 10/1990 | Rodkey et al. | 204/548 |
| 4,971,670 A | 11/1990 | Faupel et al. | 204/459 |
| 5,147,522 A | 9/1992 | Sarrine | 204/616 |
| 5,279,721 A | 1/1994 | Schmid | 204/457 |
| 5,656,145 A | 8/1997 | Nguyen et al. | 204/618 |
| 5,717,602 A | 2/1998 | Kenning | 204/457 |
| 5,865,975 A | 2/1999 | Bishop | 204/618 |
| 5,993,627 A | * 11/1999 | Anderson et al. | 204/456 |

OTHER PUBLICATIONS

"Analytical Techniques for Cell Functions—Two–Dimensional Analysis of Serum and Tissue Proteins: Multiple Isoelectric Focusing"; Anderson et al.; *Analytical Biochemistry* 85, 331–340 (1978).

* cited by examiner

*Primary Examiner*—Jill Warden
*Assistant Examiner*—John S. Starsiak, Jr.
(74) *Attorney, Agent, or Firm*—Roylance, Abrams, Berdo & Goodman, L.L.P.

(57) ABSTRACT

An automated apparatus for carrying out a first dimension electrophoresis separation of proteins and other macromolecules includes a supply magazine, an automated transferring device and an electrophoresis tank. The supply magazine includes a carousel for storing sample containers, a bar code reader, a holding device and an arm for transferring the sample container from the carousel to the bar code reader and the holding device. The transferring device includes a reciprocating pipette that is able to remove a sample from a sample container and deliver the sample to a selected gel tube in the electrophoresis tank. The tank includes a rack supporting a plurality of gel tubes and includes a chamber for containing a buffer solution in contact with one end of the gel tubes. The chamber includes a top wall with an opening having a guide surface for guiding the pipette through the chamber to the top end of the gel tubes.

76 Claims, 14 Drawing Sheets

FIRST DIMENSION ELECTROPHORESIS SEPARATION METHOD AND APPARATUS

FIELD OF THE INVENTION

The present invention is directed to a method and apparatus for performing isoelectric focusing of macromolecules, and particularly proteins. More particularly, the present invention is directed to an automated apparatus for the first dimension isoelectric focusing of proteins.

BACKGROUND OF THE INVENTION

Isoelectric focusing (IEF) is an electrophoretic technique for the analysis, separation and purification of various biological materials. Since many of the complex molecules of biological interest are amphoteric in nature, they are typically amenable to IEF separation.

Isoelectric separation is a known process that has been used for many years. An isoelectric focusing gel, such as acrylamide, is placed or polymerized in a tube and positioned in a bath with a buffer solution at each end. One buffer solution is typically a sodium hydroxide solution. The other buffer solution is typically a phosphoric acid solution. When current is applied, the two buffer solutions, together with ampholytes incorporated into the gel composition or titratable gel monomers incorporated into the gel, provide a pH gradient through the gel along the length of the tube. The sample to be analyzed is applied to a top end of the gel in a tube and an electric current is applied to an electrode in each of the buffer solutions. The molecules in the sample migrate through the gel under the influence of the electric potential until they reach their isoelectric point.

The separation of macromolecules, and particularly proteins, often is carried out by two-dimensional electrophoresis separations. The two-dimensional electrophoresis separation typically involves the sequential separation by isoelectric focusing of a sample in a gel tube followed by slab gel electrophoresis. The isoelectric focusing process is often referred to as first dimension separation. Slab gel electrophoresis, often referred to as second dimension separation, utilizes an electrophoresis gel molded between two glass plates. A gel strip or cylinder in which the protein sample has been resolved by the first dimension isoelectric focusing is placed along one edge of the slab gel. The proteins are then allowed to migrate through the gel slab under an applied voltage.

Charged detergents, such as sodium dodecyl sulfate, contained in the slab gel bind to the protein molecules. The detergents tend to unfold the protein molecules into rods having a length proportional to the length of the polypeptide chain and thus proportional to the molecular weight of the polypeptide. A protein complexed with a charged detergent is highly charged, which causes the protein-detergent complex to move in an applied electric field. When the slab gel, such as a polyacrylamide gel, functions as a sieve, the movement of the longer and higher molecular weight molecules is retarded compared to the shorter, lower molecular weight molecules.

Electrophoresis separation is generally labor intensive since numerous samples are run simultaneously. Generally, the gel tubes are prepared and placed in a suitable tank of buffer solutions. The protein samples are then manually placed on the end of a gel tube. When hundreds of protein samples are prepared daily for isoelectric focusing, the manual steps significantly increase the time requirements for performing the first dimension separation. Accordingly, there is a need in the industry for improved methods and devices for conducting first dimensional isoelectric focusing.

SUMMARY OF THE INVENTION

The present invention is directed to an apparatus for the electrophoresis separation of macromolecules and particularly proteins. More particularly, the invention is directed to an apparatus for first dimensional isoelectric focusing of proteins and other macromolecules.

Accordingly, a primary object of the invention is to provide an automated apparatus for preparing samples for electrophoresis separation.

Another object of the invention is to provide an automated apparatus for sequentially transferring a biological sample from a sample container to a gel tube for performing electrophoresis separation of the sample.

A further object of the invention is to provide an automated apparatus for transferring a biological sample from a sample container to a gel tube where the sample container is identified and selected from a container supply magazine.

Another object of the invention is to provide an automated apparatus for electrophoresis separation including a sample container magazine having a holding device for holding a sample container while a sample is being removed.

A further object of the invention is to provide an automated apparatus for electrophoresis separation including a computer controlled arm having a pipette for piercing a septum in a sample container and removing a sample from the container.

Still another object of the invention is to provide an automated apparatus for electrophoresis separation including a computer controlled arm having a pipette, and a sample container holding device for holding the container while the pipette penetrates and is withdrawn from a septum in a sample container.

Another object of the invention is to provide an automated apparatus for transferring a plurality of sample solutions to a respective gel tube and recording and tracking the location of the samples.

A further object of the invention is to provide an automated apparatus for transferring a plurality of sample solutions to a respective gel tube, wherein the apparatus includes a pipette mounted on an arm that is movable vertically for withdrawing a sample from a container and for dispensing a sample to a gel tube.

Another object of the invention is to provide an automated apparatus for electrophoresis separation having a movable robotic arm and a pipette that is movable from a sample withdrawing position to a sample dispensing position.

A further object of the invention is to provide an automated apparatus for electrophoresis separation having a movable robotic arm, where movement of the arm actuates a holding device for holding a sample container while a sample is withdrawn from the sample container.

Another object of the invention is to provide a rack for supporting a plurality of gel tubes for electrophoresis separation, wherein the rack includes a guide for guiding a pipette to a gel tube.

Still another object of the invention is to provide a rack for supporting a plurality of gel tubes, where the rack includes a top and bottom wall defining a chamber, a top wall having a plurality of inlets having a guide surface, and the bottom wall having a plurality of openings with a guide surface aligned with a respective inlet in the top wall for guiding a pipette through said chamber to a respective gel tube.

A further object of the invention is to provide a rack for supporting a plurality of gel tubes for electrophoresis separation including a pair of electric contacts received in a pair of complementary recesses in a gel tank for positioning the rack in a predetermined location in said tank.

Another object of the invention is to provide an electrophoresis separation apparatus having a computer for controlling electric power supply to the gel tanks and for the acquisition of run data for quality control.

The foregoing objects and advantages of the invention are basically attained by providing an automated first dimensional electrophoresis separation apparatus comprising: an electrophoresis assembly including a tank, a rack positionable in the tank, a plurality of gel tubes containing an electrophoretic gel and being supported by the rack. Each of the tubes has a first open end and second open end. The rack includes a chamber for containing a first buffer solution and is in communication with the first end of the tubes. The tank is dimensioned for containing a second buffer solution in contact with the second end of the tubes. An electrical power source is connected to a first electrode in the chamber for contacting the first solution and a second electrode in the tank for contacting the second solution. The apparatus contains a supply magazine for containing a plurality of sample containers where each sample container contains a sample to be subjected to electrophoresis. The apparatus also contains a transferring device for sequentially removing a sample from a preselected sample container and transferring the sample to a first end of a respective gel tube, and a microprocessor for controlling the transferring device and automatically controlling the transfer of the samples to the respective gel tubes.

The objects of the invention are further attained by providing an automated electrophoresis apparatus comprising: an electrophoresis assembly including a tank, a rack removably positioned in the tank, a plurality of gel tubes containing an electrophoretic gel and being supported by the rack, each of the tubes having a first open end and second open end, the rack having a chamber for containing a first buffer solution in contact with the first end of the tubes, the tank being dimensioned for containing a second buffer solution in contact with the end of the tubes, and an electric power source having a first electrode in the chamber for contacting the first solution and a second electrode in the tank for contacting the second solution; a supply magazine for containing a plurality of sample containers, each sample containing a sample to be subjected to electrophoresis separation; a movable arm having a pipette, a vacuum source operatively connected to the pipette, and a pressure source operatively connected to the pipette, the arm being movable from a first position where the pipette removes a sample from a preselected sample container to a second position where the pipette dispenses the sample to a preselected gel tube; and a microprocessor connected to the arm for controlling movement of the arm and actuating the vacuum source when the pipette is in the first position, and to actuate the pressure source when the pipette is in the second position to sequentially transfer a sample from the sample containers to a respective gel tube.

The objects of the invention are still further attained by providing an electrophoresis assembly comprising: a tank for containing a buffer solution, the tank having at least one side wall with a top end having at least two spaced-apart apertures therein; a rack removably positioned in the tank, the rack having an upper end, a lower end, a chamber formed in the upper end for containing a second buffer solution, the chamber having a top wall and a bottom wall, the top wall and the bottom wall having a plurality of spaced-apart aligned openings, and at least two spaced-apart pins complementing the apertures in the side wall of the tank and for orienting the rack in a predetermined location in the tank; and a plurality of gel tubes, each of the tubes having a first end received in a respective opening in the bottom wall of the chamber.

The objects of the invention are yet further attained by providing a rack for supporting a plurality of gel tubes in an electrophoresis assembly, the rack comprising: at least one support member for supporting the rack in an electrophoresis tank; a top wall having a plurality of spaced-apart openings; a bottom wall having a plurality of spaced-apart openings aligned with a respective opening in the top wall; and at least one side wall, where the at least one side wall, top wall and bottom wall form a chamber for containing an electrophoresis buffer solution.

The objects of the invention are further obtained by providing a method for automated first dimensional electrophoresis separation comprising the steps of: providing a plurality of samples in sample containers; robotically removing the samples from the sample containers; robotically delivering the samples to one end of a respective isoelectric focusing gel; and controlling an electrical current to the isoelectric focusing gel and separating portions of the samples within the isoelectric focusing gel.

The objects of the invention are yet further obtained by providing an automated first dimensional electrophoresis separation apparatus comprising: an electrophoresis assembly including a tank, a rack positionable in the tank, a plurality of gel tubes containing an isoelectric focusing gel and being supported by the rack, the rack including at least two alignment pins, the alignment pins being received in alignment apertures formed in a portion of the tank for insuring precise positioning of the rack in the tank; a supply magazine for containing a plurality of sample containers, each sample container containing a sample to be subjected to electrophoresis; a transferring device for sequentially removing a sample from a pre-selected sample container and transferring the sample to a first end of a respective gel tube; and a microprocessor for controlling the transferring device and automatically controlling the transfer of the samples to the respective gel tubes.

The objects of the invention are still further obtained by providing an automated first dimensional electrophoresis separation apparatus comprising: an electrophoresis assembly including a tank, a rack positionable in the tank, a plurality of gel tubes containing an isoelectric focusing gel and being supported by the rack; a supply magazine for containing a plurality of sample containers, each sample container containing a sample to be subjected to electrophoresis separation; a transferring device for sequentially removing a sample from a preselected sample container and transferring the sample to a first end of a respective gel tube; a container holding member for holding a pre-selected sample container while the transferring device removes a sample from the sample container; and a microprocessor for controlling the transferring device and automatically controlling the transfer of the samples to the respective gel tubes.

The objects, advantages and salient features of the invention will become apparent to one skilled in the art in view of the following detailed description of the invention in conjunction with the annexed drawings which form a part of this original disclosure.

BRIEF DESCRIPTION OF THE DRAWINGS

The following is a brief description of the drawings, in which.

DETAILED DESCRIPTION OF THE INVENTION

Figure 1:
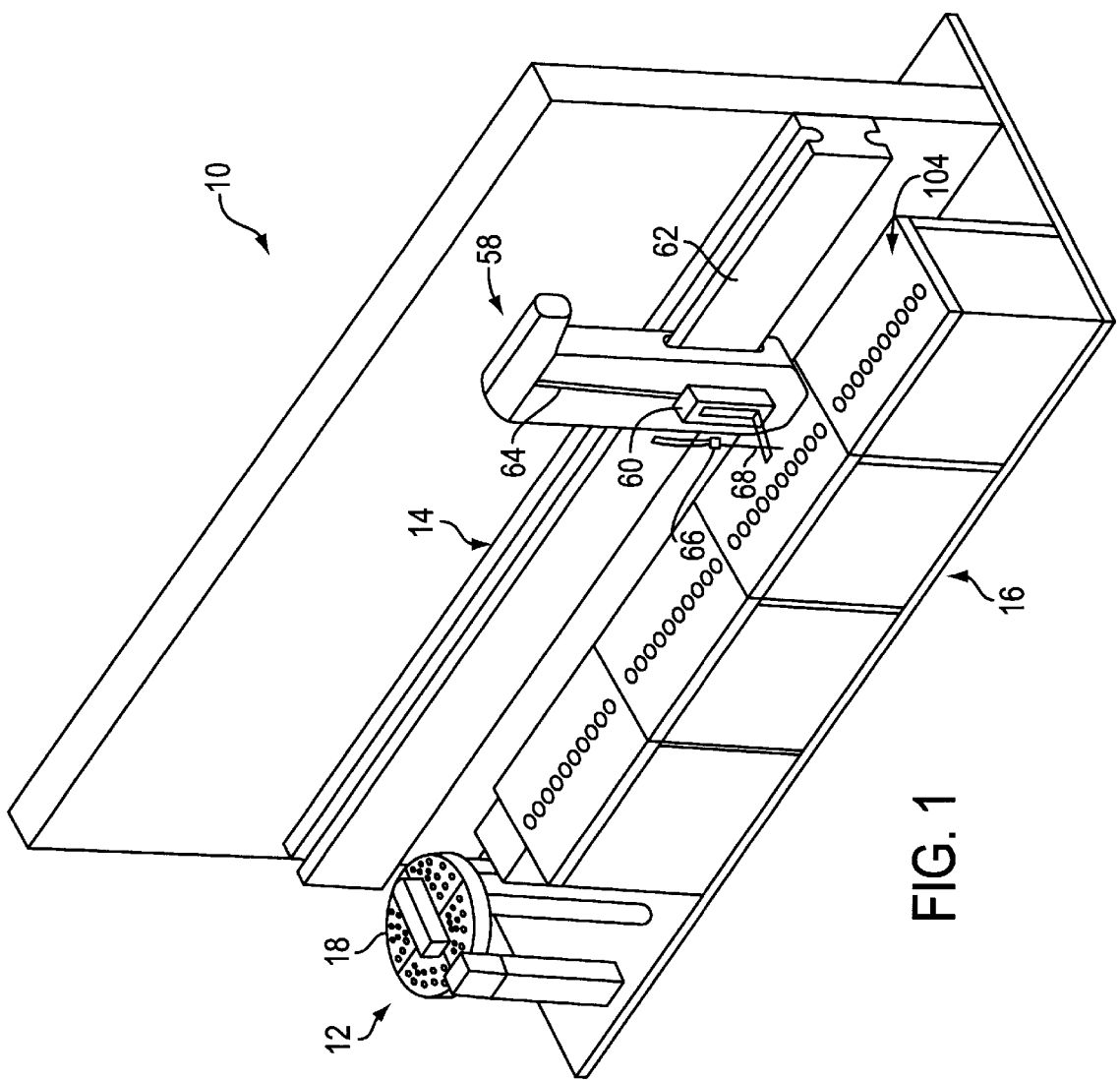
FIG. 1 is a perspective view of the apparatus of the invention showing the gel tanks, sample supply magazine and transferring device for transferring a sample from a sample container to a gel tube in a gel tank.

The present invention is directed to a method and apparatus for performing first dimension electrophoresis separation of a biological sample. In particular, the invention is directed to an automated apparatus for loading a plurality of samples into a respective tube containing an isoelectric gel and simultaneously performing electrophoresis separation of the sample.

The method and apparatus of the invention are used primarily in sequence with a second dimension electrophoresis separation step for isolating and recovering specific proteins in a sample. As discussed hereinafter in greater detail, the first dimension separation utilizes an electrophoresis gel in a tube having each end placed in a buffer solution. An electric potential is applied to cause the proteins to migrate through the gel. The electrophoresis gel and the buffer solutions are standard materials, such as IPG gels, as known in the art of electrophoresis.

The biological samples to be subjected to the electrophoresis separation are typically protein samples. The protein samples are usually solubilized in an aqueous, denaturing solution such as 9 m urea, 2% NP-40 (a non-ionic detergent), 2% of a pH 8–10.5 ampholyte mixture and 1% dithiothreitol (DTT). The urea and NP-40 dissociate complexes of proteins with other proteins and with DNA and RNA. The ampholyte mixture establishes a high pH outside the range where most proteolytic enzymes are active and prevent modification of the sample protein by the ampholyte. The ampholyte further complexes with DNA present in the nuclei of sample cells and allows DNA-binding proteins to be released while preventing the DNA from swelling into a viscous gel that interferes with IEF separation. The dithiothreitol reduces the disulfide bonds in the proteins and allows them to unfold and assume an open structure for separation. Tissue samples are often solubilized by homogenizing in a solubilizing solution. The resulting mixture is centrifuged to remove insoluble material.

The method and apparatus of the invention are used in the first dimension separation of a two dimensional separation system. The first dimension separation uses an isoelectric focusing gel, such as an acrylamide gel with a catalyst, focusing compounds and cross-linking agents. The gel is placed in a tube, such as a glass tube, having open ends. The bottom end of the tube is placed in a $H_3PO_4$ buffer solution and the top end placed in a sodium hydroxide buffer solution to establish a pH gradient along the gel. The sample material is applied to the top end of the tube and allowed to migrate through the gel under the influence of an electrical potential. Generally, an electric current of about 1200 volts is applied between the upper and lower buffer solutions for about 20 hours. The isoelectric focusing gel and buffer solutions are conventional materials known in the art for first dimension separation.

Referring to the drawings, the electrophoresis apparatus 10 includes a sample supply magazine 12, an automated robotic transferring assembly 14 and a plurality of buffer tanks 16. Buffer tanks 16 contain several tubes that contain an isoelectric focusing gel. As discussed hereinafter, transferring assembly 14 automatically removes a sample from supply magazine 12 and robotically transfers and delivers the sample to the tubes within tanks 16.

Figure 2A:
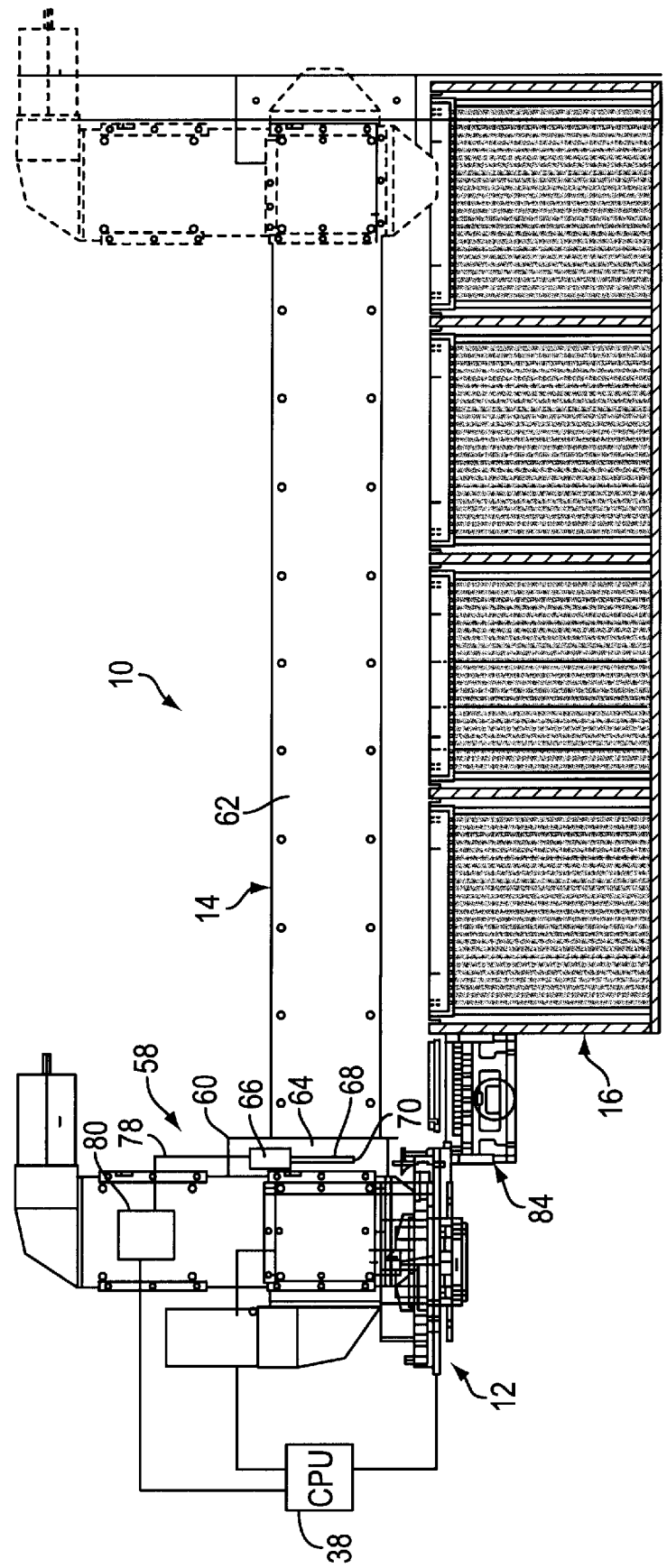
FIG. 2A is a front view of the apparatus of FIG. 1.
Figure 2B:
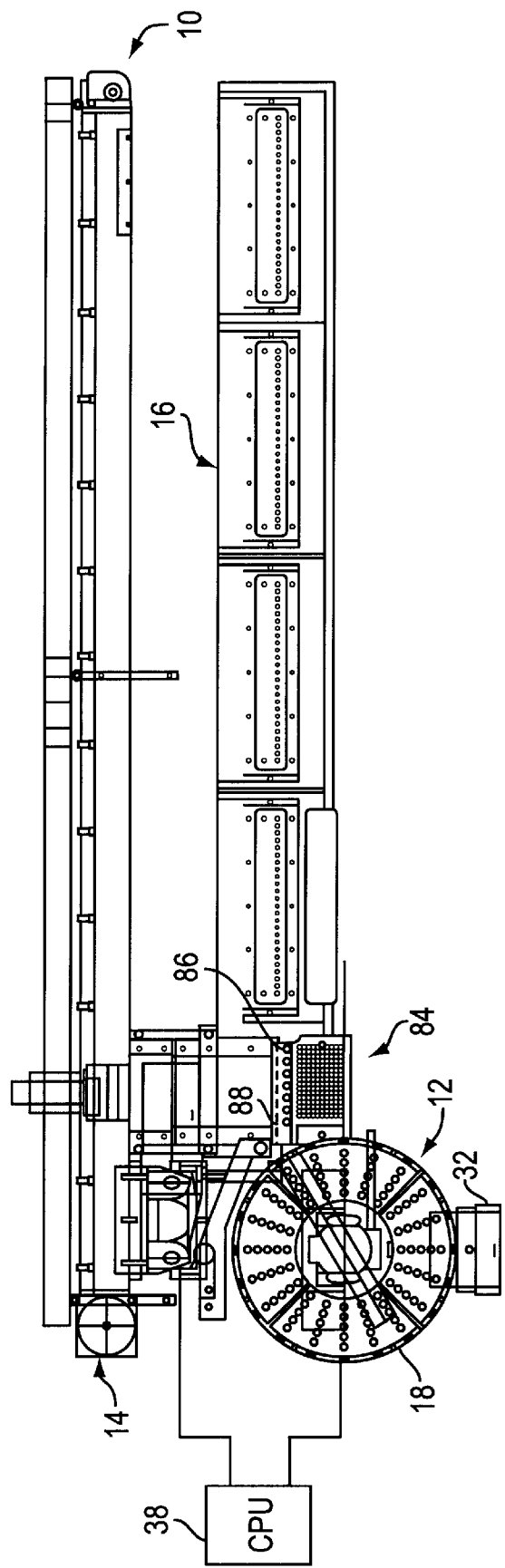
FIG. 2B is a top view of the apparatus of FIG. 1.
Figure 3:
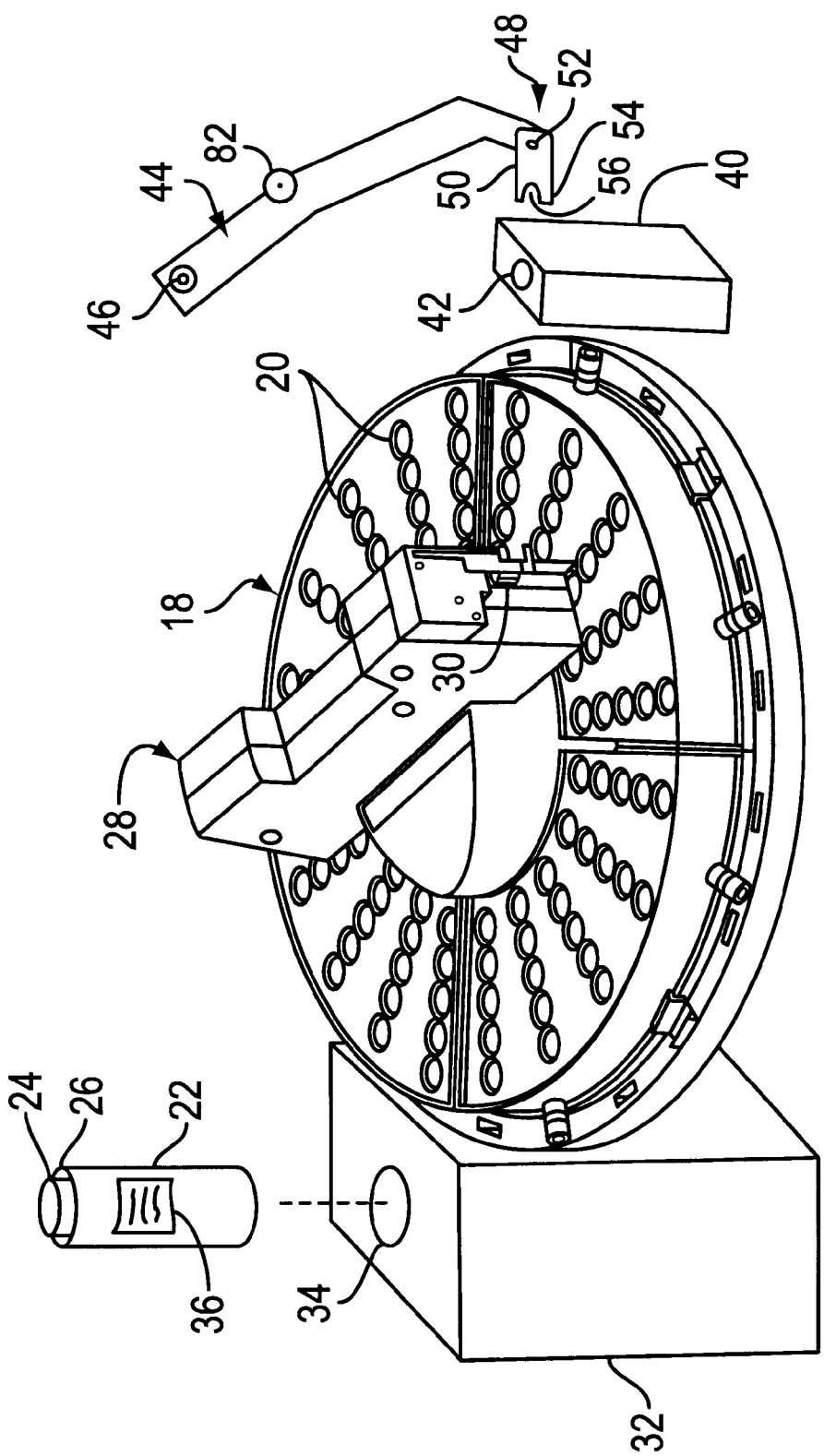
FIG. 3 is a perspective view of the supply magazine showing the carousel, bar code reader and sample container holding device.

Referring to FIGS. 2B and 3, supply magazine 12 in a preferred embodiment is a carousel 18 having a plurality of wells 20 for storing a plurality of sample containers 22. Each sample container 22 is preferably a glass or plastic vial having an internal volume sufficient to contain a biological sample. A closure 24 is coupled to the open end 26 of sample container 22 to seal container 22 and prevent contamination of the sample and to prevent the sample from escaping. In a preferred embodiment, closure 24 is a flexible septum that can be pierced by a needle or pipette to withdraw a sample from sample container 22.

Carousel 18 includes a robotic arm 28 that is able to pivot around the axis of carousel 18. Carousel 18 is also able to rotate about its axis to bring a selected sample container into position for being picked up by robotic arm 28. Robotic arm 28 is also able to reciprocate in a radial direction with respect to carousel 18. Robotic arm 28 includes a gripping member 30 that reciprocates in an up and down direction for gripping and removing a sample container 22 from a well 20 of carousel 18. An example of this type of carousel is manufactured by the Hewlett-Packard Corporation as the HP Automatic Liquid Sampler, Model HP 18596B.

In one embodiment of the invention, supply magazine 12 includes a bar code reader 32 positioned adjacent carousel 18 for electronically reading, storing and indexing sample information. A suitable bar code reader is made by the Hewlett-Packard Corporation, such as the reader sold as model HPG 1926A. In alternative embodiments, other devices can be used for recording and storing information relating to the samples. Bar code reader 32 includes a well 34 for receiving a sample container 22. Sample container 22 preferable includes a label 36 having a bar code or other indicia that can be read by bar code reader 32. Supply magazine 12 is connected to a central processing control unit 38 (CPU) such as a microprocessor for controlling the movement of robotic arm 28 and recording information from bar code reader 32. Central processing unit 38 actuates robotic arm 28 and carousel 18 to select a predetermined sample container 22 and remove sample container 22 from well 20 and transfer the container to bar code reader 32. Bar code reader 32 records the information on label 36 and stores the information for tracking and identifying a sample throughout the separation process. Bar code reader 32 is operatively connected to central processing unit 38 for recording and tracking samples. Supply magazine 12 also includes a sample container holding device 40 having a well 42 for receiving a sample container 22 from arm 28.

Figure 4:
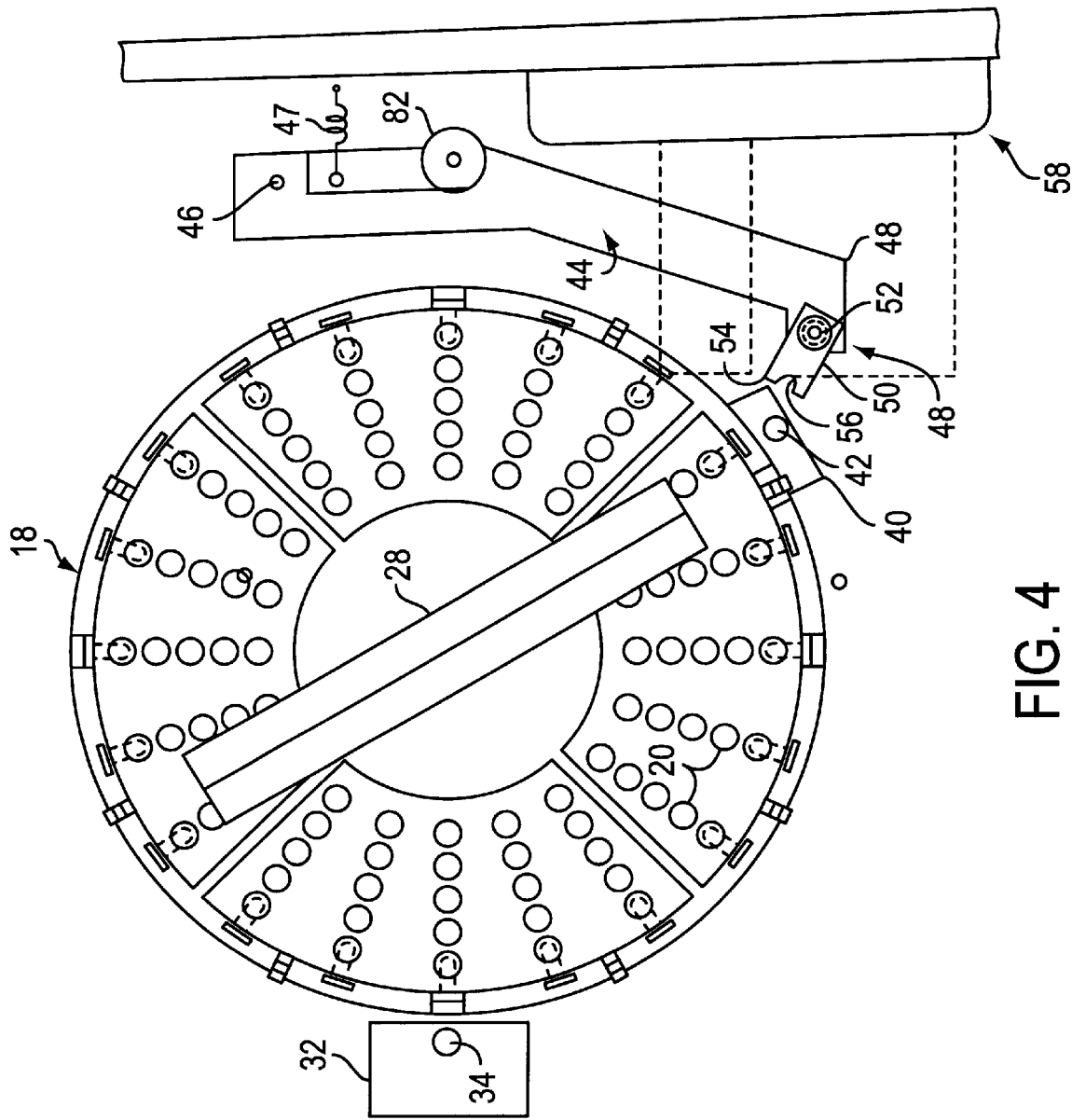
FIG. 4 is a partial top view of the apparatus of FIG. 1 showing the carousel and container retaining arm in a first position.

As shown in FIGS. 3 and 4, holding device 40 is positioned adjacent carousel 18. Arm 28 is able to reciprocate a suitable length for placing a sample container 22 into well 42. Holding device 40 preferably includes a suitable mechanism for retaining sample container 22 in well 42 while the biological sample is removed from container 22.

Figure 5:
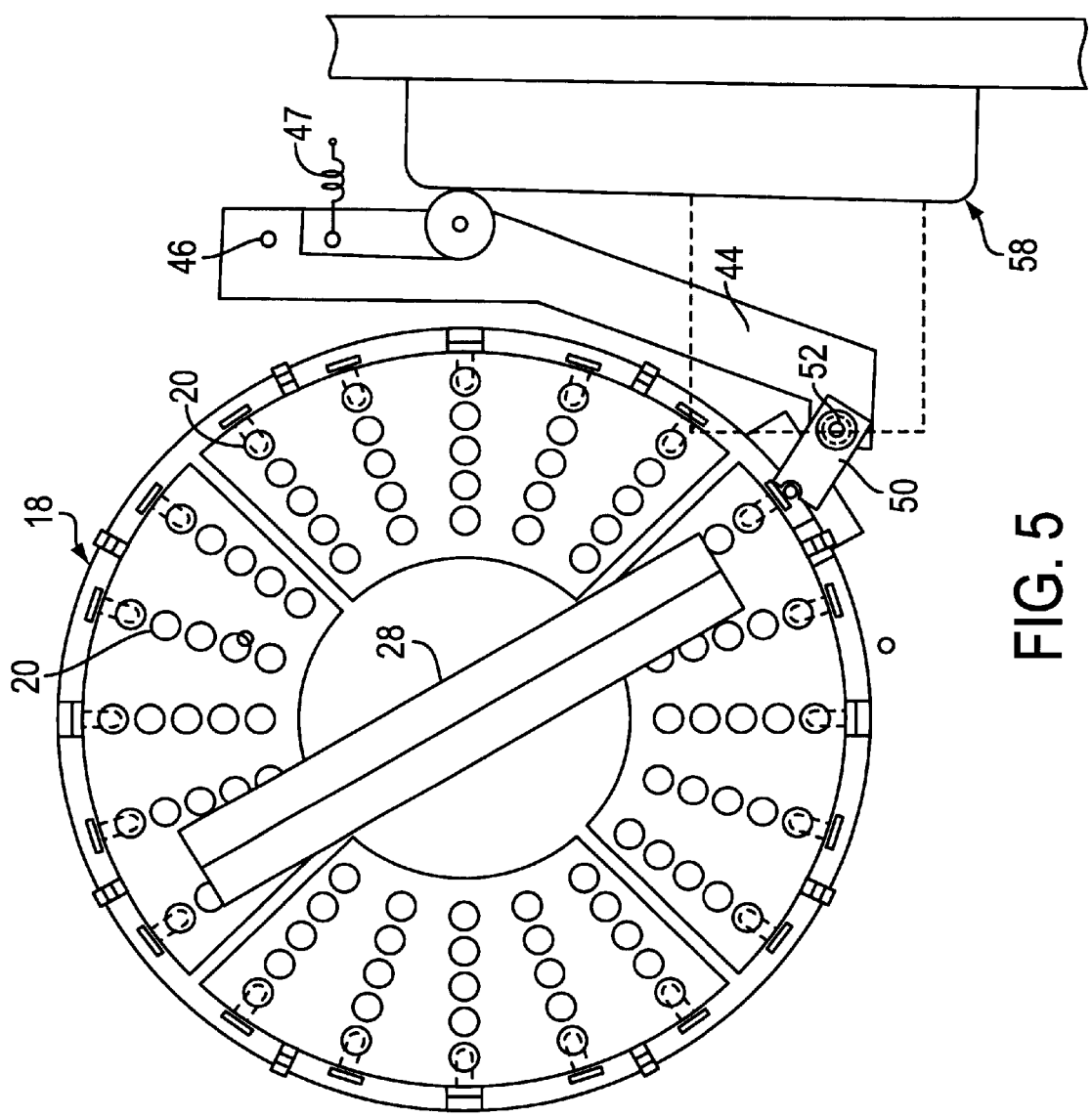
FIG. 5 is a partial top view of the apparatus of FIG. 1 showing the carousel and retaining arm in a second position for retaining a sample container in a holder.

In a preferred embodiment shown in FIGS. 3, 4 and 5, the retaining mechanism is a retaining arm 44 provided on supply magazine 12 to hold sample container 22 within well 42. Retaining arm 44 is mounted adjacent supply magazine 12 by a pivot pin 46 to allow retaining arm 44 to pivot about the axis of pin 46 from a first position shown in FIG. 4 to a retaining position shown in FIG. 5. A spring 47 biases arm 44 away from supply magazine 12. Retaining arm 44 includes an operating end 48 to hold sample container 22 in well 42. In the illustrated embodiment, end 48 has an end plate 50 coupled thereto. End plate 50 is attached to retaining arm 44 by a fastener 52. Preferably, fastener 52 is a threaded screw or bolt that can be tightened to fix the position of end plate 50 with respect to retaining arm 44 and can be loosened to enable end plate 50 to pivot to enable adjustment of end plate 50 to a desired location. In this manner, end plate 50 can be adjusted on retaining arm 44 to provide proper alignment of end plate 50 with respect to holding device 40 and well 42.

As shown in FIG. 4, end plate 50 has an outer edge 54 with a substantially U-shaped recess 56. End plate 50 has a dimension sufficient to overlie the top end of a sample container 22 when received in well 42 while exposing a portion of closure 24 of sample container 22 through recess 56 for piercing closure 42 by a piercing member to remove a sample from container 22. In alternative embodiments, the retaining mechanism can be a gripping device able to grip the side walls of container 22, or a vacuum source for drawing a vacuum sufficient to hold sample container 22 within well 42. In other embodiments, plate 50 can be fixed to arm 44 or integrally formed therewith. Arm 44 can also be operated by a motor or piston and cylinder assembly, such as a pneumatic piston. A switch can be actuated by transferring assembly 14 to actuate the operating motor or pneumatic cylinder.

Figure 6:
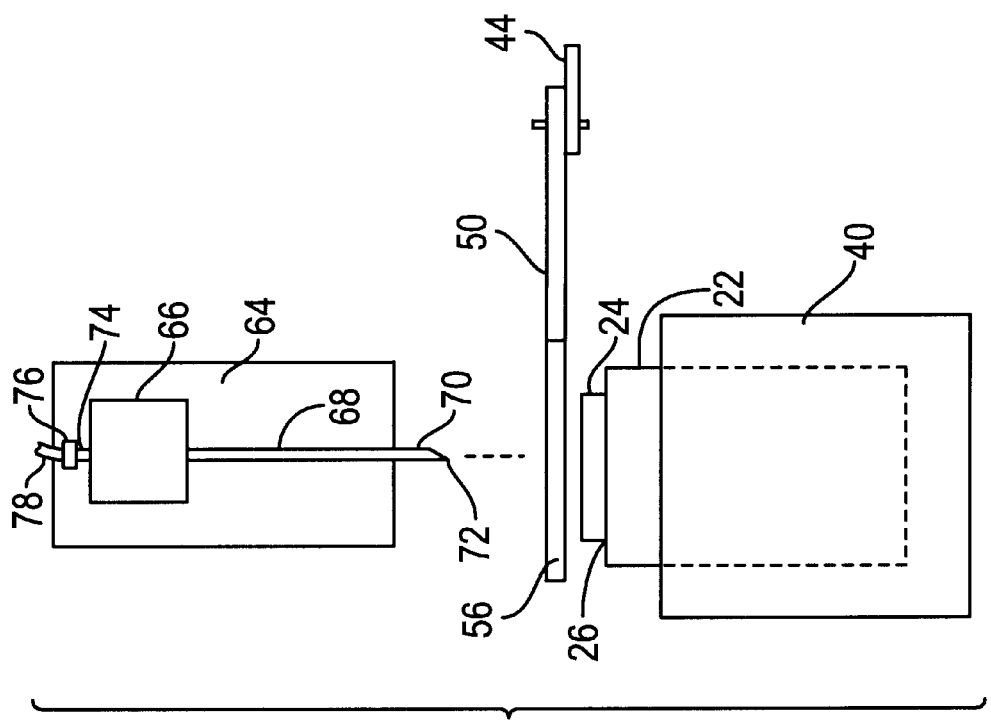
FIG. 6 is a partial front view of the sample container holding device showing the retaining arm positioned over the container.
Figure 7:
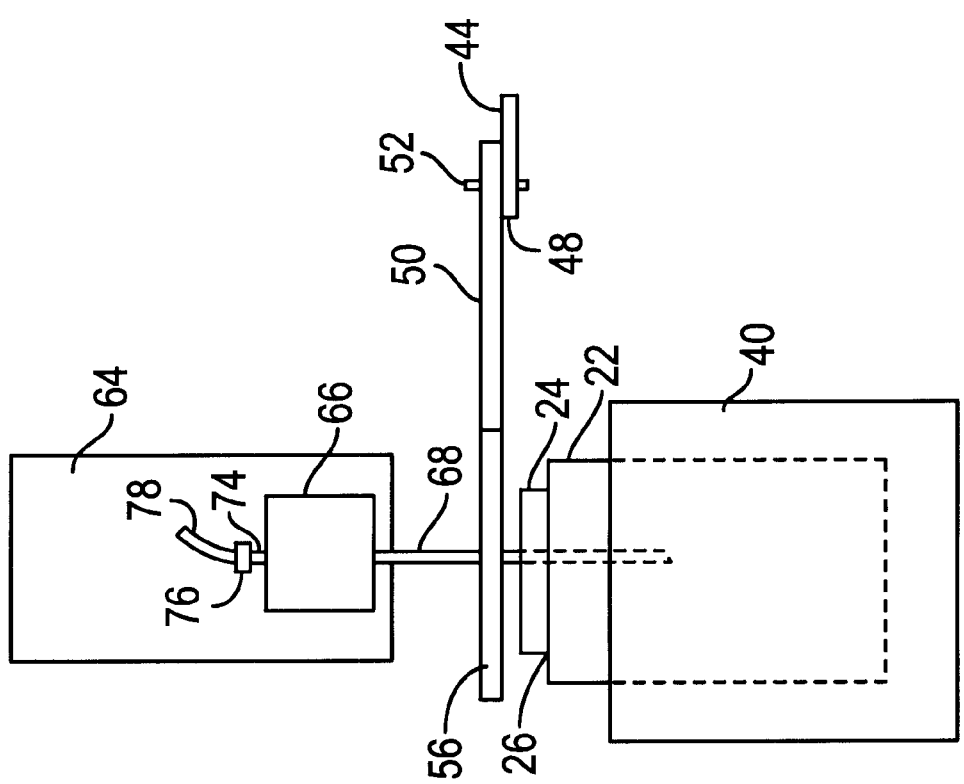
FIG. 7 is a partial front view of the sample container holding device showing the retaining arm holding the sample container in place while the pipette penetrates the septum of the sample container.

Referring to FIG. 1, automated transferring assembly 14 is positioned adjacent supply magazine 12 and includes a movable arm assembly 58. Movable arm assembly 58 includes a main body 60 that is movable along a horizontal track 62. Transferring assembly 14 includes a drive mechanism driven by a suitable motor for moving body 60 along track 62. The drive mechanism can be, for example, a gear or chain drive assembly connected to the motor for moving main body 60 at a controlled speed and precisely controlling the position of main body 60 along track 62. Body 60 is provided with a vertical track 64 in which an operating arm 66 is received and movable in a vertical direction. Operating arm 66 supports a pipette 68 oriented vertically and coupled to arm 66 for reciprocating movement with arm 66. Pipette 68 is a micropipette having a generally cylindrical shape with an axial passage extending therethrough. A distal end 70 includes a sharpened tip 72 as shown in FIG. 6. A top end 74 includes a coupling 76 attached to a flexible tube 78. Tube 78 is connected to a pump 80 for selectively applying a negative pressure to pipette 68 for drawing a vacuum to collect a sample and for applying a positive pressure to dispense the sample from the pipette. In preferred embodiments, pipette 68 is a metal syringe needle-like device having an internal volume sufficient to contain a biological sample for a first dimension electrophoresis separation.

As shown in FIG. 1, transferring assembly 14 is also coupled to central processing unit 38 for controlling the movement of movable arm assembly 58 and the actuation of pump 80. In operation, sample containers containing a biological sample are provided in carousel 18. Arm 28 of carousel 18 selects a sample container 22 from carousel 18 and places sample container 22 in bar code reader 32 where the sample identification and other information is recorded and stored in control unit 38. Arm 28 of carousel 18 then transfers sample container 22 from bar code reader 32 to holding device 40. As shown in FIG. 2, main body 60 of transferring assembly 14 slides along horizontal track 62 from a position adjacent holding device 40 to a respective buffer tank 16 and a designated tube mounted in tank 16. Retaining arm 44 of supply magazine 12 is positioned in the horizontal path of main body 60 as main body 60 moves along track 62 in the direction of supply magazine 12.

As shown in FIGS. 3 and 4, retaining arm 44 includes a bearing 82, such as a roller bearing, for contacting main body 60. Retaining arm 44 also includes a biasing member, such as a spring 47, to bias retaining arm 44 outwardly from carousel 18 to the position shown in FIG. 4. As main body 60 is moved to the first end of horizontal track 62, main body 60 contacts bearing 82 causing retaining arm 44 to pivot about pivot pin 46 so that the end plate 50 overlies the sample container 22 as shown in FIG. 5 with U-shaped recess 56 oriented over closure 24. Movable arm 58 is lowered to a position where pipette 68 pierces closure 24 of sample container 22. Pump 80 is actuated to withdraw a desired amount of a sample from container 22 into pipette 68. Movable arm 58 is then raised to withdraw pipette 68 from sample container 22. End plate 50 of retaining arm 44 overlies sample container 22 to hold sample container 22 in holding device 40 while pipette 68 is withdrawn. Retaining arm 44 prevents sample container 22 from being lifted upward when pipette 68 is raised to the upper position.

Main body 60 is then moved along horizontal track 62 a selected position corresponding to a designated gel tube in a tank 16. As body 60 is moved away from supply magazine 12, body 60 disengages retaining arm 44, allowing arm 44 to pivot outward from carousel 18. Movable arm 58 is then lowered to a position at the top end of the designated tube and pump 80 is actuated to dispense the sample from pipette 68 onto the top end of the gel tube. Movable arm 58 is then raised and moved along horizontal track to a rinsing station 84 for rinsing sample residue from pipette 68.

Rinsing station 84 includes a container 86 containing a rinsing liquid such as distilled water. Movable arm 58 is lowered to insert pipette 68 into container 86 where a sufficient amount of the rinsing liquid is drawn into pipette 68 to rinse the inner surfaces of pipette 68. Pipette 68 is then raised and moved to a position above a discharge container 88 where the rinsing liquid is discharged.

Movable arm 58 and pipette 68 are then moved back to the position shown in FIG. 5 and the steps repeated to transfer another sample from a sample container to a designated gel tube. The sequence of steps is repeated until the desired samples from the sample containers are transferred to a designated gel tube. Control unit 38 controls the movement of the supply magazine and transferring assembly 14 and records the location of each sample to identify a sample with a particular gel tube.

Referring to FIGS. 8–13, buffer tanks 16 have a bottom wall 100 and side walls 102 for containing a first buffer solution. A rack 104 supporting a plurality of gel tubes 106 is dimensioned to fit within tank 16 as shown in FIG. 6. In one embodiment of the invention, bottom wall 100 of tank 16 can include an optional spacing member such as a pair of blocks 108 for positioning rack 104 within tank 16 in a predetermined location. Preferably, tank 16 is fixed to a support surface or positioned in a specific location with respect to assembly 14. In this manner, rack 104 and gel tubes 106 are oriented in a precise location with respect to assembly 14 so that the arm of transferring device 28 can transfer a biological sample from a sample container 22 to a designated gel tube in successive runs without the need to recalibrate the apparatus after each run. In a preferred embodiment, gel tubes 106 are oriented in a straight line aligned with the pipette 68 so that pipette 68 can be positioned above each tube 106 by selectively moving main body 60 of transferring device 14 along track 62. Pipette 68 can then be lowered along straight track 64 to dispense the sample to a gel tube.

Figure 12:
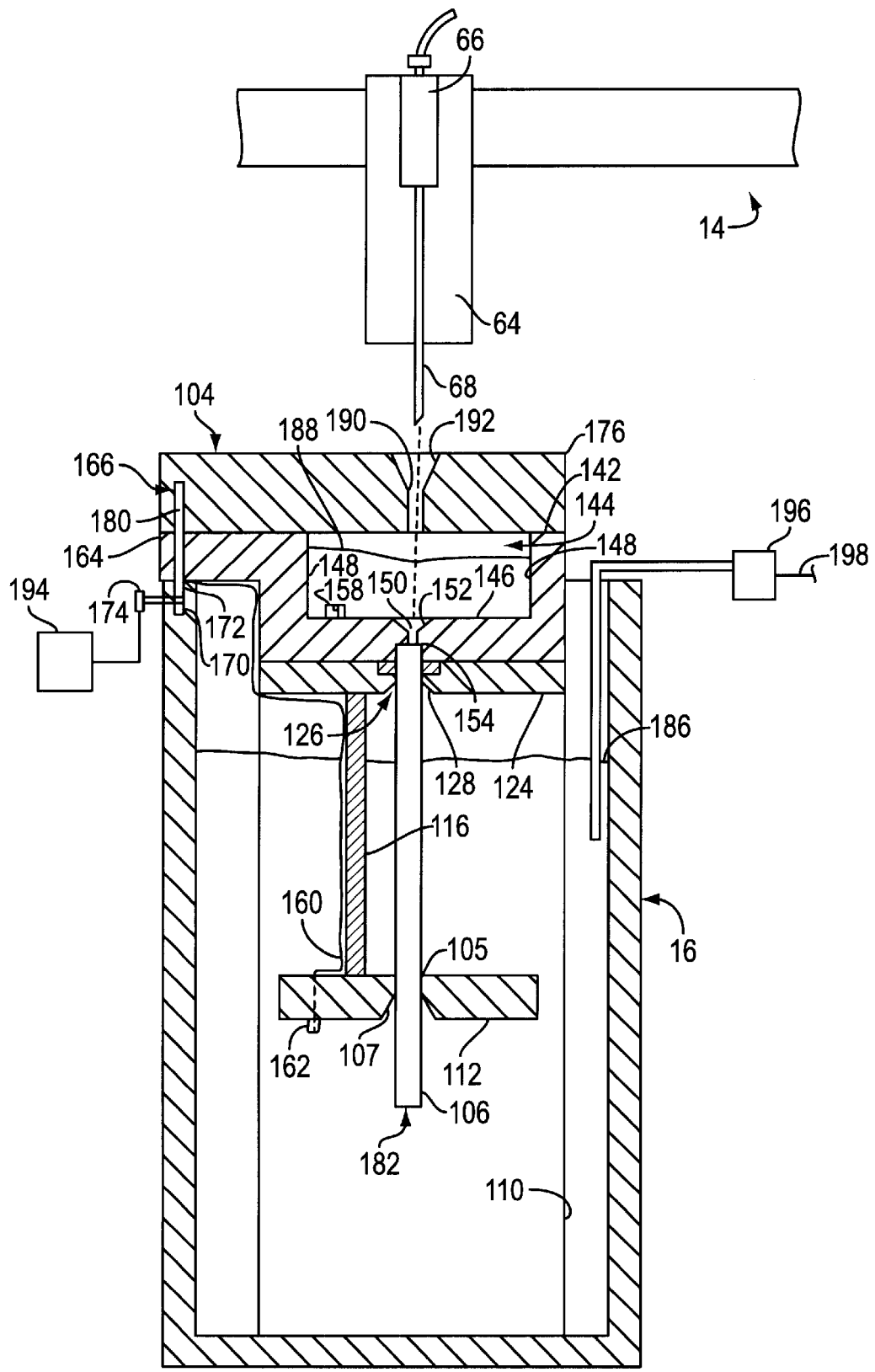
FIG. 12 is a partial cross-sectional view of the tank and gel tube rack showing the pipette positioned above the rack.

Rack 104 in the embodiment illustrated, has a pair of side walls 110 spaced apart a sufficient distance to enable rack 104 to fit within tank 16. Side walls 110 function as a support for rack 104 when rack 104 is positioned in tanks 16. A lower brace 112 extends between side walls 110 to stabilize rack 104. A plurality of spaced apart holes 105 having a conical surface 107 are formed in brace 112 to support tubes 106 as shown in FIG. 12. Preferably, brace 112 is a planar member extending perpendicular to side walls 110 to lie in a substantially horizontal plane when rack 104 is positioned in tank 16. Brace 112 is coupled to side walls 110 by screws 114 or other suitable fasteners. A vertical brace 116 extends between side walls 110 and is coupled thereto by screws 118 or other suitable fasteners to further stabilize rack 104.

Figure 8:
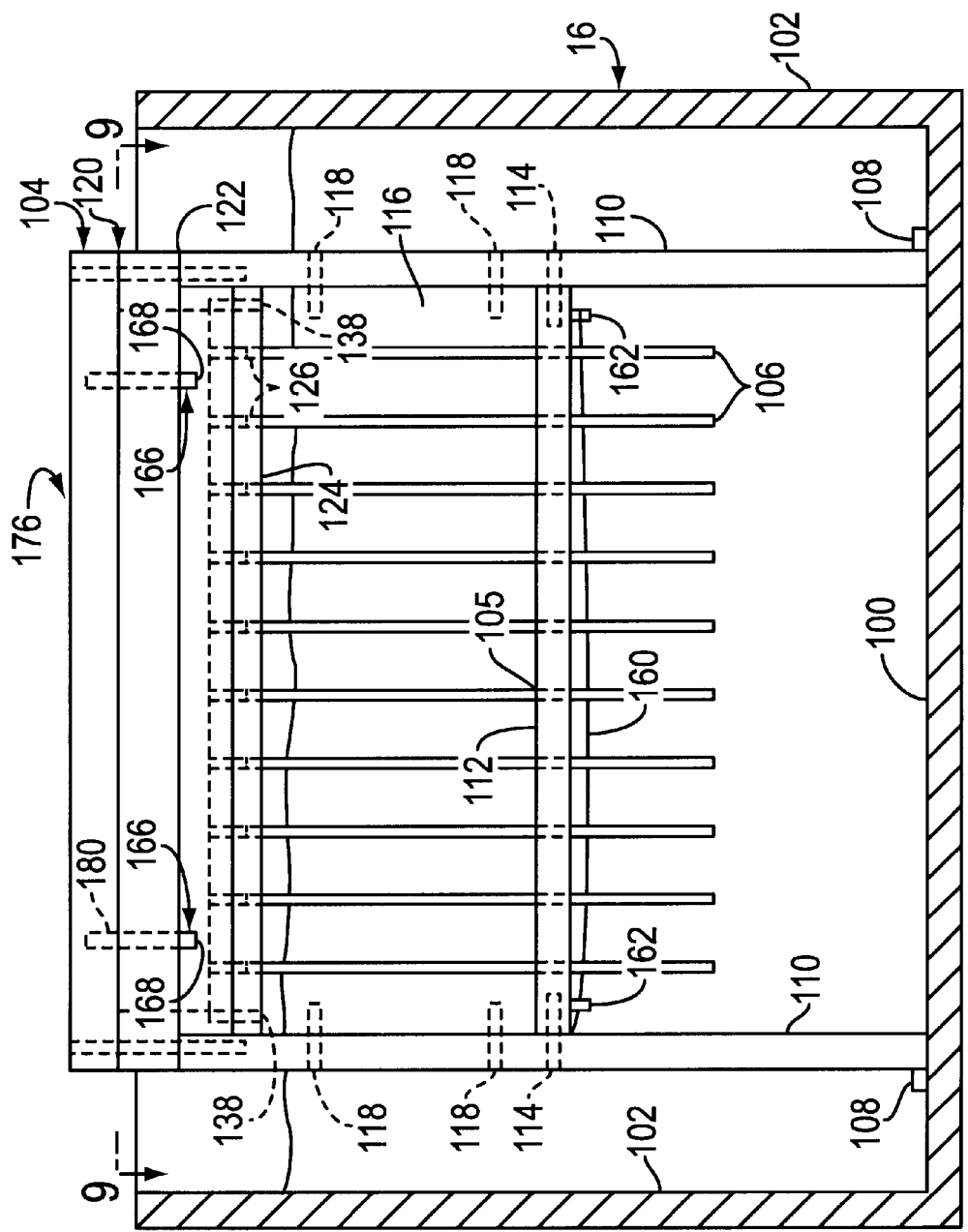
FIG. 8 is a front elevational view of the gel tube rack positioned in the tank in a preferred embodiment of the invention.
Figure 9:
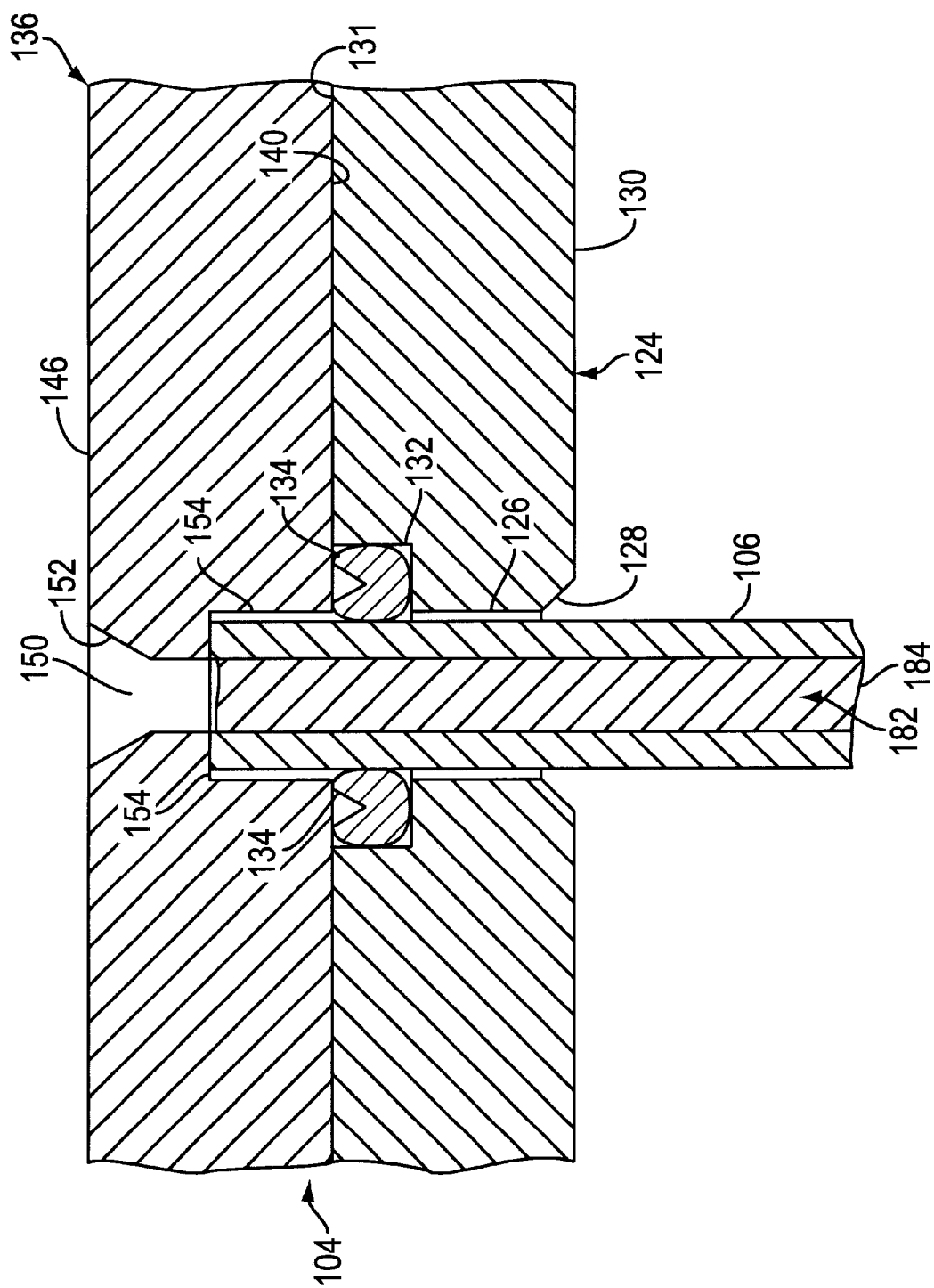
FIG. 9 is an enlarged area in cross section of the rack showing the gasket for holding the gel tube in place.

Rack 104 includes a trough assembly 120 coupled to a top end 122 of side walls 110. Trough assembly 120 includes a lower plate 124, a middle block 136 and a top plate 176. Trough 120 includes a chamber that is dimensioned to contain a sufficient amount of a second buffer solution for conducting electrophoresis separation as known in the art. Trough 120 includes a lower plate 124 that is attached to side walls 110. Lower plate 124 is oriented in a substantially horizontal position and parallel to lower brace 112. As shown in FIGS. 8 and 9, lower plate 124 is provided with a plurality of spaced apart openings 126 that are dimensioned to receive gel tubes 106. Openings 126 have a conical recess 128 on a bottom face 130 of plate 124 for guiding tubes 106 into openings 126. Plate 124 also includes an annular recess 132 on a top face 131 surrounding each opening 126 for receiving an annular gasket 134 having a substantially V-shaped cross-section.

Middle block 136 of trough 120 is coupled to lower plate 124 by screws 138. Block 136 has a bottom face 140 for mating with plate 124. A top face 142 of block 136 includes a recessed area 144 defining an upper chamber or tank for containing the second buffer solution. Recessed area 144 has a bottom face 146 and side walls 148. In a preferred embodiment, bottom face 146 is substantially parallel to top face 142 and side walls 148 are perpendicular to bottom face 146 and top face 142. Recessed area 144 includes a plurality of openings 150 extending from bottom face 146 of recessed area 144 to bottom face 140 of middle block 136. Openings 150 have a conical shaped inlet end 152 formed in face 146 and an annular recess 154 in bottom face 140. Annular recess 154 is dimensioned to receive the end of gel tube 106.

Figure 10:
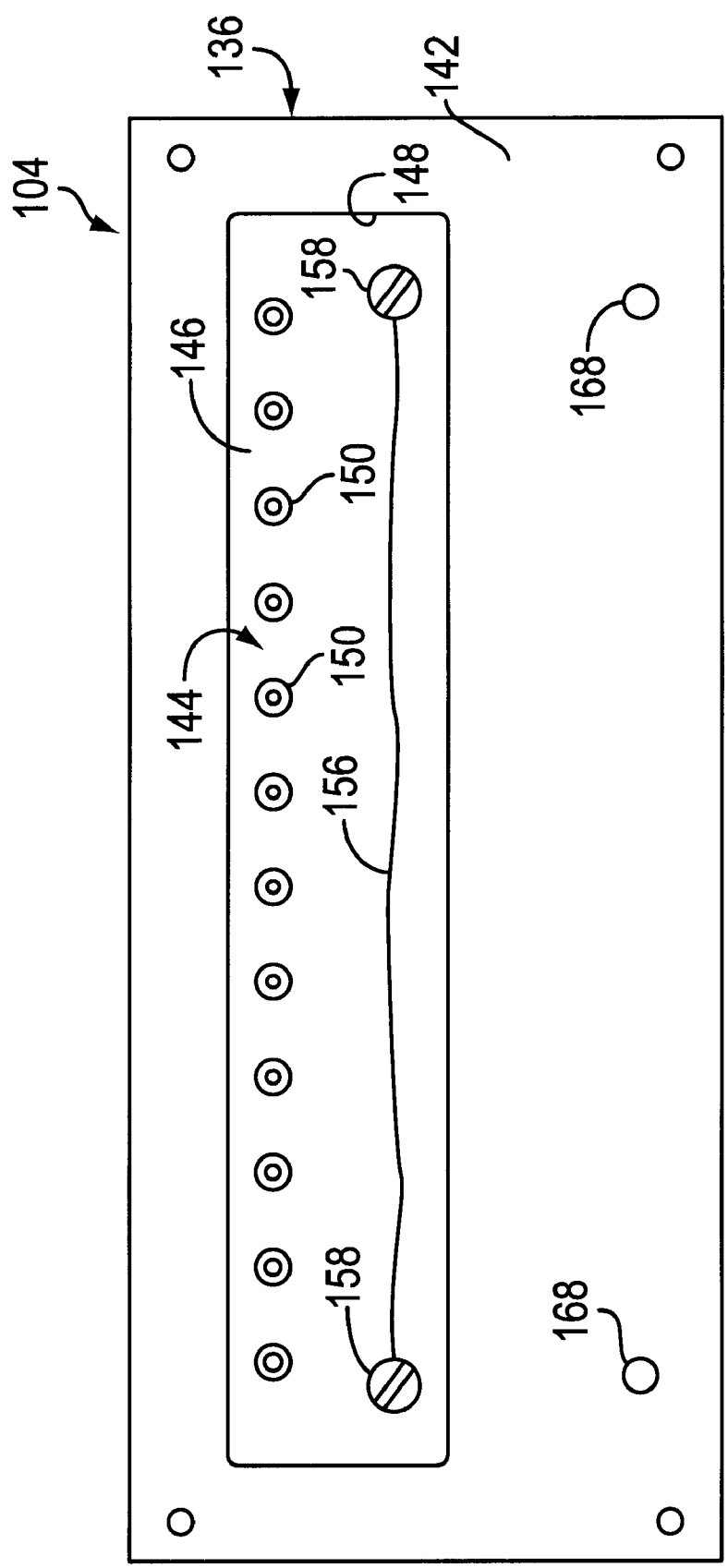
FIG. 10 is a top view of the gel tube rack of FIG. 8 with the top cover removed and showing the chamber for a buffer solution.

As shown in FIG. 10, a first electrode 156 is provided within recessed area 144 and secured in place by screws 158. In a preferred embodiment of the invention, first electrode 156 is a wire that extends substantially the length of recessed area 144. As shown in FIG. 9, a second electrode 160 extends along brace 112 and is secured in place by mounting screws 162.

Figure 11:
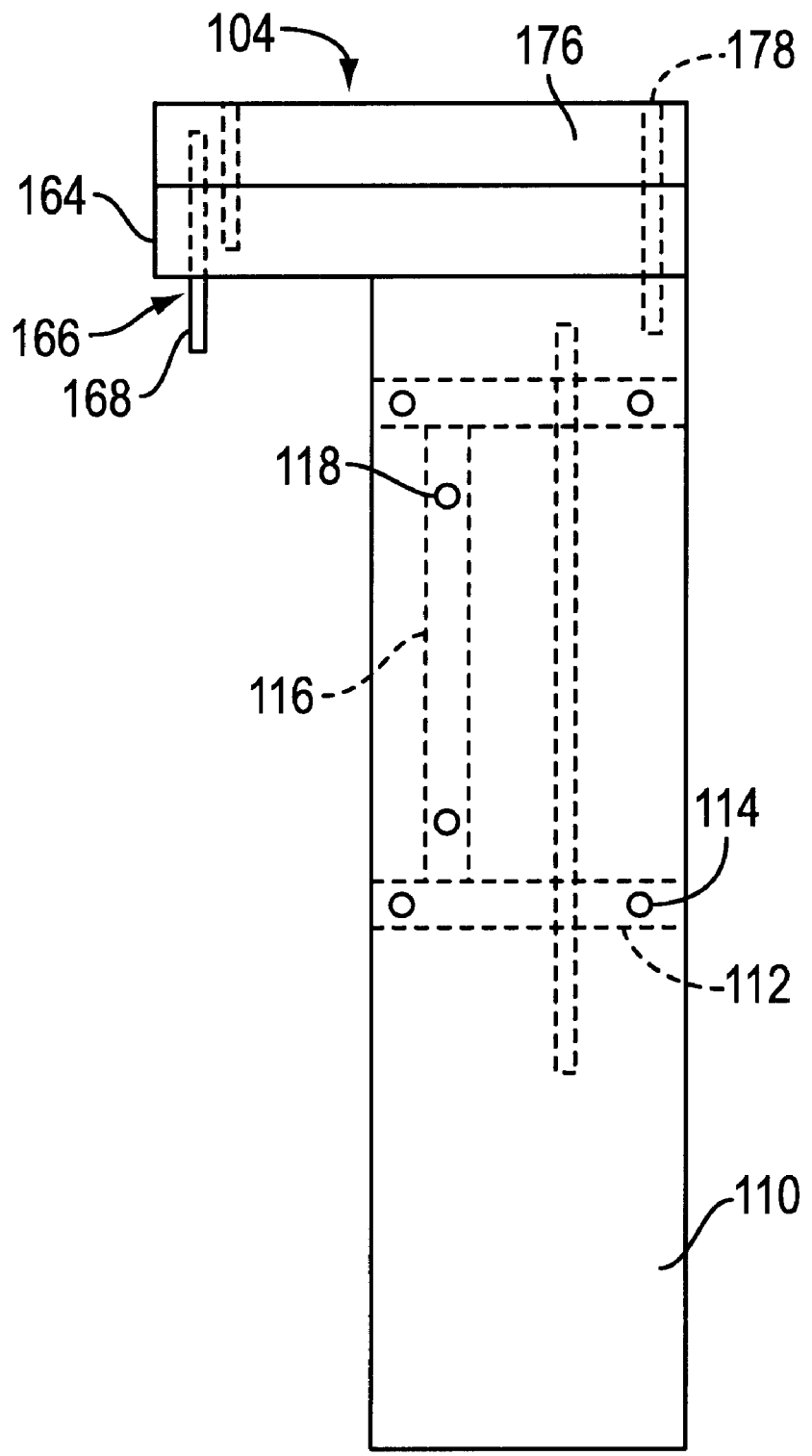
FIG. 11 is a side view of the rack of FIG. 8.
Figure 13:
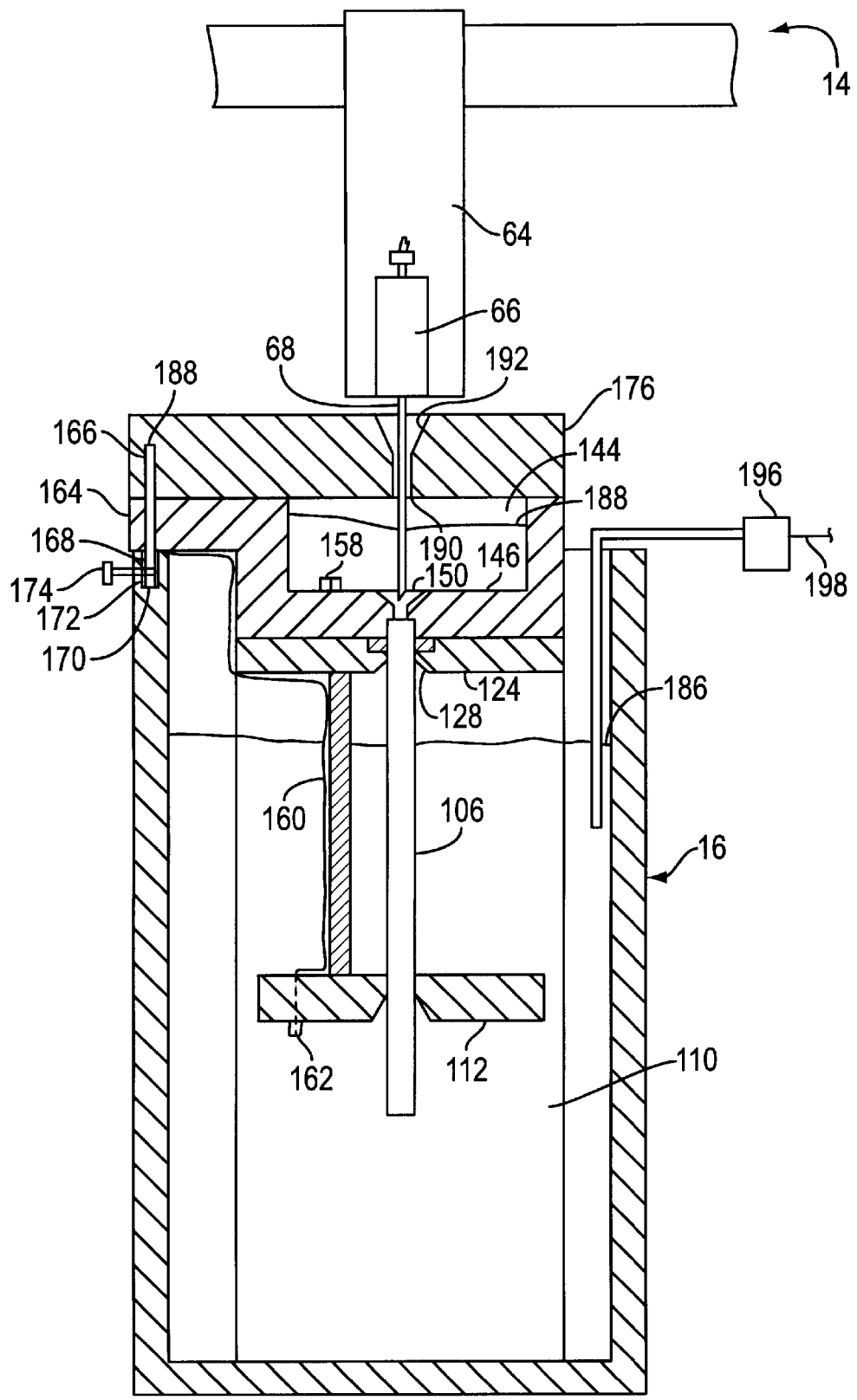
FIG. 13 is a partial cross-sectional view of the tank and gel tube rack showing the pipette inserted through the openings in the rack for delivering a sample to the gel tube.

Block 136 includes a ledge portion 164 extending outwardly from a top end in a direction generally parallel to bottom face 140. As shown in FIGS. 11 and 13, ledge 164 is spaced from the bottom end of side walls 110 a distance corresponding substantially to the height of side walls 102 of tank 16. In this manner, ledge 164 is able to rest on an upper end of side wall 102 with side walls 110 of rack 104 supported by bottom wall 100 of tank 16. In a preferred embodiment, at least two alignment pins 166 extend downwardly through ledge 164. Each pin 166 has a lower portion 168 that is received in a respective recess 170 formed in the top end of side wall 102. Recesses 170 in side wall 102 are located to orient rack 104 in a specific location within tank 16. Since tank 16 is mounted in a fixed position, rack 104 can be removed from tank 16 and replaced in the same orientation for transferring assembly 14 to consistently deliver a sample to a gel tube supported by rack 104. Pin 166 can be a cylindrical shape or square. In a preferred embodiment, pins 166 are spring loaded pins commonly referred to as "banana clips".

In a preferred embodiment, each recess 170 in the top end of side walls 102 include a metal sleeve 172 that is connected to a coupling member 174 as shown in FIG. 13. Pins 166 are made of metal or other electrically conducting material for making electrical contact with sleeves 172. Electrodes 156 and 160 are connected to a respective pin 166 so that rack 104 can be positioned in tank 16 to provide an electrical connection between coupling member 174 and electrodes 156 and 160. Coupling members 174 are connected to a suitable electric power source to apply an electric potential to electrodes 156 and 160.

Trough 120 includes a top wall 176 that is removably coupled to top face 142 of block 136 by pins 178 as shown in FIG. 11. Top wall 176 is provided with apertures 180 complementing alignment pins 166. As shown in FIG. 8, top wall 176 is coupled to block 136 and oriented by alignment pins 166.

Top wall 176 also includes a plurality of spaced apart apertures 190 aligned with the openings 150 in bottom face 146. A top face of top wall 176 includes conical shaped recesses 192 axially aligned with apertures 190 to form guiding surfaces for directing the pipette into apertures 190.

Referring to FIG. 9, gel tubes 106 have a cylindrical shape with a central passage 182 and open ends. The inner dimension of gel tubes 106 can range from 0.5 mm to about 2 mm and can be about 20 cm long. Gel tubes 106 are standard gel tubes as known in the art. An electrophoresis gel 184 is placed in gel tubes 106 to substantially fill gel tubes 106 as shown in FIG. 9 by known techniques. The gel forming materials can be placed in the tube and polymerized to form the gel. The gels can be IPG gels or other isoelectric focusing gels as known in the art.

The electrophoresis separation process of the invention is carried out using the apparatus 10. Gel tubes 106 containing a gel 184 are mounted in rack 104 by sliding gel tubes 106 through the holes 105 in lower brace 112. The conical surface 107 of the holes 105 in lower brace 112 provides a guiding surface for guiding gel tubes 106 through brace 112. Gel tubes 106 are then inserted into openings 126 of lower plate 124 using conical recesses 128 as a guide. The top end of gel tube 106 is seated in recess 132 of bottom face 130 as shown in FIG. 11. Annular gasket 134 is dimensioned to provide a fluid tight seal around gel tube 106 to prevent fluids from passing from trough 120 into tank 16. A gel tube 106 is positioned in each respective opening in rack 104.

A buffer solution 186, such as a phosphoric acid solution, is provided in tank 16 and rack 104 is positioned in gel tank 16 with alignment pins 166 received in recesses 170 of tank 16. Buffer solution 186 is maintained at a level above the lower end of gel tubes 106 and electrode 160. A second buffer solution 188, such as a sodium hydroxide solution, is placed in trough 120 to a sufficient level to cover the top end of gel tubes 106 and first electrode 156. Top wall 176 is coupled to block 136 to close the chamber.

After rack 104 and gel tubes 106 are positioned in tank 16, transferring assembly 14 is actuated to transfer a biological sample from supply magazine 12 to a respective gel tube 106. Pipette 68 withdraws a biological sample from a sample container 22 as previously discussed. Main body 60 of assembly 14 moves along track 62 to a location above a respective gel tube 106 as shown in FIG. 9. Top wall 176 of trough 120 is provided with a plurality of apertures 190 corresponding to each gel tube in rack 104. Apertures 190 have a conical top end 192 for guiding pipette 186 through aperture 190. The conical surface 192 of aperture 190 forms a guide surface to compensate for misalignment of pipette 168 with aperture 190. Although microprocessor 38 and the consistent location of racks 104 and gel tubes 106 usually provide proper alignment of pipette 168, misalignment can occur as a result of the pipette tip being bent or distorted. Repeated piercing of the septum of the sample containers can bend pipette 168, thereby causing the tip to be misaligned with the openings in rack 104. Conical surfaces 152 and 192 can assist in aligning and directing the tip of pipette 168 to the proper location above gel tubes 106.

As shown in FIGS. 9 and 11, apertures 190 of top wall 176 are axially aligned with openings 150 and gel tube 106. Movable arm 58 of assembly 14 is moved downward to insert the lower end of pipette 68 to the top end of gel tube 106. Conical surface 152 of opening 150 serves to guide pipette 68 to gel tube 106. Pipette 68 then dispenses the biological sample onto the top end of gel 184 in gel tube 106. Pipette 68 is removed from rack 104 and returned to supply magazine 112 to repeat the process.

After a biological sample is placed on the top end of each gel tube 106 in rack 104, coupling members 174 are connected to a suitable power source 194 for applying an electric current to the electrodes and the buffer solutions. The electric current causes the various components of the biological sample to migrate through the gel tube as in standard first dimension electrophoresis separation. After a predetermined period of time, gel tubes 106 are removed from rack 104 and the gels are transferred to a second dimension separation apparatus as known in the art.

In preferred embodiments, power source 194 is operatively connected to central processing unit 38. Central processing unit 38 controls the voltage applied to the electrodes 156, 160 of tank 16. The current and voltage fluctuations are measured, continuously monitored and recorded over time throughout the duration of the isoelectric focusing to provide information for quality control. The recorded voltage and current can then be plotted as a function of time throughout the process.

A temperature control device 196 is preferably provided with tanks 16 as shown in FIG. 12 for measuring and adjusting the temperature of buffer solution 186 in tank 16. Temperature control device 196 is able to provide heating or cooling to tank 16 to maintain the temperature within a predetermined range. Preferably, temperature control device 196 is connected to and controlled by central processing unit 38 through a connection 198.

While various embodiments of the invention have been illustrated, it will be understood by those skilled in the art that additions and modifications can be made without departing from the scope of the invention as set forth in the appended claims.

What is claimed is:

1. An automated first dimensional electrophoresis separation apparatus comprising:
    an electrophoresis assembly including a tank, a rack positionable in said tank, a plurality of gel tubes containing an electrophoretic gel and being supported by said rack, each of said tubes having a first open end and second open end, said rack including a chamber for containing a first buffer solution and being in communication with said first end of said tubes, said tank being dimensioned for containing a second buffer solution in contact with said second end of said tubes, and an electrical power source having a first electrode in said chamber for contacting said first solution and a second electrode in said tank for contacting said second solution;
    a supply magazine for containing a plurality of sample containers, each sample container containing a sample to be subjected to electrophoresis;
    a transferring device to sequentially remove a sample from a preselected sample container and transfer said sample to a first end of a respective gel tube; and
    a microprocessor connected to said transferring device to automatically control the transfer of said samples to said respective gel tubes.

2. The apparatus of claim 1, wherein said transferring device comprises a robotic arm operatively connected to said microprocessor.

3. The apparatus of claim 1, wherein said microprocessor controls said robotic arm to sequentially remove a sample from said sample containers and dispense said sample sequentially to a first end of a respective gel tube.

4. The apparatus of claim 3, wherein said robotic arm includes a pipette for removing said samples from said containers and for dispensing said samples to said respective gel tube.

5. The apparatus of claim 4, wherein said sample containers include a septum and said robotic arm is movable to a position whereby said pipette pierces said septum for withdrawing a sample from said sample containers.

6. The apparatus of claim 5, wherein said transferring device further comprises a vacuum source connected to said pipette for withdrawing a sample from a sample container, and a pressure source connected to said pipette for dispensing a sample to said gel tube.

7. The apparatus of claim 3, wherein said robotic arm includes a syringe needle operatively connected to said microprocessor for removing said samples from said container and for dispensing said samples to said respective gel tube.

8. The apparatus of claim 3, wherein said transferring device comprises a substantially horizontal track extending from said supply magazine to said electrophoresis device, said robotic arm being movable along said track, and said robotic arm being movable in a substantially vertical direction to a first position for removing a sample from a sample container and to a second position for dispensing said sample to a gel tube.

9. The apparatus of claim 1, wherein said supply magazine includes a detecting and recording device for detecting a sample container and recording a sample identification, said detecting and recording device being connected to said microprocessor for identifying and recording information corresponding to a sample transferred to a gel tube.

10. The apparatus of claim 9, wherein said sample containers include a bar code and said detecting and recording device is a bar code reader.

11. The apparatus of claim 1, wherein said supply magazine is a carousel.

12. The apparatus of claim 1, wherein said supply magazine includes an arm operatively coupled to said microprocessor, said arm being movable from a first position for retrieving a preselected sample container to said detecting and recording device.

13. The apparatus of claim 1, wherein said supply magazine is a carousel rotatable about an axis to provide access by said transferring device to said preselected sample container, and wherein said microprocessor is operatively connected to said carousel for rotating said carousel to a predetermined location.

14. The apparatus of claim 1, wherein said supply magazine comprises a container holding member for holding a preselected sample container while said transferring device removes a sample from said sample container.

15. The apparatus of claim 14, wherein said supply magazine further comprises a retaining device for retaining said preselected sample container in said holding member while said transferring device removes a sample from said sample container.

16. The apparatus of claim 15, wherein said retaining device is a retaining arm that is movable from a first position spaced from said holding member to a second position for retaining said sample container in said holding member.

17. The apparatus of claim 16, wherein said retaining arm is pivotally mounted and pivotable from said first position to said second position.

18. The apparatus of claim 16, wherein said retaining arm covers at least a portion of a top end of said sample container when in said second position for retaining said sample container in said holding member.

19. The apparatus of claim 16, wherein said retaining arm includes an operating end having a recessed area therein, said operating end of said retaining arm overlying a top end of said sample container when said retaining arm is in said second position.

20. The apparatus of claim 16, wherein said transferring device comprises a substantially horizontal track extending from said supply magazine to said electrophoresis device and a robotic arm movable along said track to a first position for removing a sample from a preselected sample container to a second position for dispensing said sample to said gel tube, and wherein movement of said robotic arm toward said supply magazine moves said retaining arm to said second position.

21. The apparatus of claim 20, wherein said retaining arm is pivotally mounted and said first position of said retaining arm is in a path of said robotic arm whereby said robotic arm contacts said retaining arm when moved toward said supply magazine and pivots said retaining arm to said second position.

22. The apparatus of claim 1, wherein said rack is removable from said tank and said rack comprises a support for supporting said rack within said tank, and a chamber for containing said second buffer solution, said chamber comprising a bottom wall and a top wall.

23. The apparatus of claim 22, wherein said bottom wall of said chamber includes a plurality of spaced-apart openings, and said first end of said gel tubes is fitted in a respective opening in said bottom wall whereby said first end of each of said gel tube is in communication with said chamber.

24. The apparatus of claim 23, wherein said bottom wall includes a sealing member associated with each of said openings for sealing an outer surface of said gel tubes with respect to said bottom wall.

25. The apparatus of claim 23, wherein said top wall of said compartment includes a plurality of spaced-apart openings aligned with a respective opening in said bottom wall.

26. The apparatus of claim 25, wherein said openings in said top wall of said chamber have a conical shaped upper end for guiding said transferring device to a respective opening in said bottom wall of said chamber.

27. The apparatus of claim 26, wherein said openings in said bottom wall of said chamber have a conical shaped upper end for guiding said transferring device to said gel tubes.

28. The apparatus of claim 22, wherein said rack comprises first and second electrically conductive posts, and said tank comprises two complementing recesses for receiving said posts to position said rack in a predetermined position in said tank.

29. The apparatus of claim 28, wherein said recesses in said tank include an electrical contact for electrically connecting said posts to said power source, and wherein said first electrode is connected to said first post and said second electrode is coupled to said second post.

30. The apparatus of claim 29, wherein said posts extend in a substantially upward direction with respect to an upper end, and said top wall includes two complementing recesses for receiving said posts and positioning said top wall in a predetermined location with respect to said bottom wall.

31. An automated electrophoresis apparatus comprising:
an electrophoresis assembly including a tank, a rack removably positioned in said tank, a plurality of gel tubes containing an electrophoretic gel and being supported by said rack, each of said tubes having a first open end and second open end, said rack having a chamber for containing a first buffer solution in contact with said first end of said tubes, said tank being dimensioned for containing a second buffer solution in contact with said second end of said tubes, and an electric power source having a first electrode in said chamber for contacting said first solution and a second electrode in said tank for contacting said second solution;
a supply magazine for containing a plurality of sample containers, each sample containing a sample to be subjected to electrophoresis separation;
a movable arm having a pipette, a vacuum source operatively connected to said pipette, and a pressure source operatively connected to said pipette, said arm being movable from a first position where said pipette removes a sample from a preselected sample container to a second position where said pipette dispenses said sample to a preselected gel tube; and a microprocessor connected to said arm for controlling movement of said arm and actuating said vacuum source when said pipette is in said first position, and to actuate said pressure source when said pipette is in said second position to sequentially transfer a sample from said sample containers to a respective gel tube.

32. The apparatus of claim 31, wherein said microprocessor is operatively connected to said arm to insert said pipette into a sample container, actuate said vacuum source to remove a sample from said sample container, and to withdraw said pipette from said sample container.

33. The apparatus of claim 32, wherein said sample containers include a septum and said arm is movable to a position whereby said pipette pierces said septum.

34. The apparatus of claim 31, wherein said apparatus comprises a substantially horizontal track extending from said supply magazine to said electrophoresis device, said arm being movable along said track, and wherein said arm is movable in a substantially vertical direction with respect to said track to said first position for removing a sample from a sample container and to said position for dispensing said sample to a gel tube.

35. The apparatus of claim 31, wherein said supply magazine includes a bar code reader for detecting a sample container and recording a sample identification, said bar code reader being connected to said computer for recording a location of a sample in a gel tube.

36. The apparatus of claim 35, wherein said supply magazine includes a carousel, and an arm operatively coupled to said microprocessor, said arm being movable from a first position for retrieving a preselected sample container and transferring said sample container to said bar code reader.

37. The apparatus of claim 33, wherein said supply magazine comprises a container-holding member for holding a preselected sample container while said pipette removes a sample from said sample container, and a retaining arm for retaining said preselected sample container in said holding member while said pipette is removed from said sample container.

38. The apparatus of claim 37, wherein said retaining arm is pivotally mounted and pivotable from said first position to said second position.

39. The apparatus of claim 37, wherein said retaining arm covers at least a portion of a top end of said sample container when in said second position for retaining said sample container in said holding member.

40. The apparatus of claim 37, wherein said retaining arm includes an operating end having a recessed area therein, said operating end of said retaining arm overlying a top end of said sample container when said retaining arm is in said second position.

41. The apparatus of claim 37, wherein said retaining arm is pivotally mounted and said first position of said retaining arm is in a path of said arm whereby said arm contacts said retaining arm when moved to said first position and pivots said retaining arm to said second position.

42. The apparatus of claim 31, wherein said rack comprises side walls for supporting said rack within said tank, and wherein said chamber comprises a bottom wall and a top wall, said bottom wall of said chamber including a plurality of spaced-apart openings, and said first end of said gel tubes being fitted in a respective opening in said bottom wall whereby said first end of said gel tubes is in communication with said chamber.

43. The apparatus of claim 42, wherein said bottom wall includes a sealing member associated with each of said openings for sealing an outer surface of said gel tubes with respect to said bottom wall.

44. The apparatus of claim 42, wherein said top wall of said chamber includes a plurality of spaced-apart openings aligned with said openings in said bottom wall.

45. The apparatus of claim 44, wherein said openings in said top wall of said chamber have a conical shaped upper end for guiding said transferring device to a respective opening in said bottom wall of said chamber.

46. The apparatus of claim 45, wherein said openings in said bottom wall of said chamber have a conical shaped upper end for guiding said pipette to said gel tubes.

47. The apparatus of claim 40, wherein said rack comprises first and second electrically conductive posts and said tank includes two complementing recesses for receiving said posts to position said rack in a predetermined position in said tank.

48. The apparatus of claim 47, wherein said recesses in said tank include an electrical contact for electrically connecting said posts to said power source, and wherein said first electrode is connected to said first post and said second electrode is coupled to said second post.

49. The apparatus of claim 48, wherein said posts extend in a substantially upward direction to an upper end, and said top wall includes two complementing recesses for receiving said posts and positioning said top wall in a predetermined location with respect to said bottom wall.

50. An electrophoresis assembly comprising:

a tank for containing a buffer solution, said tank having at least one side wall with a top end having at least two spaced-apart apertures therein;

a rack removably positioned in said tank, said rack having an upper end, a lower end, a chamber formed in said upper end for containing a second buffer solution, said chamber having a top wall and a bottom wall, said top wall and said bottom wall having a plurality of spaced-apart aligned openings, and at least two spaced-apart pins complementing said apertures in said side wall of said tank and for orienting said rack in a predetermined location in said tank; and a plurality of gel tubes, each of said tubes having a first end received in a respective opening in said bottom wall of said chamber.

51. The assembly of claim 50, wherein at least one side wall has a top face and said spaced-apart apertures are provided in said top face.

52. The assembly of claim 51, wherein said at least two spaced-apart pins extend in a downward direction with respect to said rack for coupling with said side wall of said tank.

53. The assembly of claim 50, further comprising a first electrode in said tank and a second electrode in said chamber of said rack, wherein said electrodes are coupled to one of said pins.

54. The assembly of claim 53, further comprising an electrical contact in each of said apertures in said side wall of said tank for contacting said pins.

55. The assembly of claim 50, wherein said bottom wall includes a sealing member associated with each of said openings for sealing an outer surface of said gel tubes with respect to said bottom wall.

56. The assembly of claim 50, wherein said openings in said top wall of said chamber have a conical shaped upper end for guiding a pipette to a respective opening in said bottom wall of said chamber.

57. The assembly of claim 56, wherein said openings in said bottom wall of said chamber have a conical shaped upper end for guiding said pipette to said gel tubes.

58. The assembly of claim 50, wherein said pins are electrically conductive.

59. The assembly of claim 50, wherein said pins extend in a substantially upward direction with respect to an upper end, and said top wall includes two complementing recesses for receiving said posts and positioning said top wall in a predetermined location with respect to said bottom wall.

60. An automated first dimensional electrophoresis separation apparatus, comprising:

an electrophoresis assembly including a tank, a rack positionable in said tank, a plurality of gel tubes containing an isoelectric focusing gel and being supported by said rack, said rack including at least two alignment pins, said alignment pins being received in alignment apertures formed in a portion of said tank for insuring precise positioning of said rack in said tank;

a supply magazine for containing a plurality of sample containers, each sample container containing a sample to be subjected to electrophoresis;

a transferring device for sequentially removing a sample from a pre-selected sample container and transferring said sample to a first end of a respective gel tube; and a microprocessor for controlling said transferring device and automatically controlling the transfer of said samples to said respective gel tubes.

61. The apparatus of claim 60, further comprising an electrical power source, said electrical power source being connected to said assembly to apply an electric potential between said first end and a second end of said gel tubes.

62. An automated first dimensional electrophoresis separation apparatus, comprising:

an electrophoresis assembly including a tank, a rack positionable in said tank, a plurality of gel tubes containing an isoelectric focusing gel and being supported by said rack;

a supply magazine for containing a plurality of sample containers, each sample container containing a sample to be subjected to electrophoresis separation;

a transferring device for sequentially removing a sample from a preselected sample container and transferring said sample to a first end of a respective gel tube;

a container holding member for holding a pre-selected sample container while said transferring device removes a sample from said sample container; and a microprocessor for controlling said transferring device and automatically controlling the transfer of said samples to said respective gel tubes.

63. The apparatus of claim 62, wherein said supply magazine comprises a retaining device for retaining said pre-selected sample container in said holding member while said transferring device removes a sample from said sample container.

64. The apparatus of claim 62, wherein said retaining device is a retaining arm that is movable from a first position spaced from said holding member to a second position for retaining said sample container in said holding member.

65. The apparatus of claim 64, wherein said retaining arm is pivotally mounted and pivotable from said first position to said second position.

66. The apparatus of claim 65, wherein said retaining arm covers at least a portion of a top end of said sample container when in said second position for retaining said sample container in said holding member.

67. The apparatus of claim 64, wherein said retaining arm includes an operating end having a recessed area therein, said operating end of said retaining arm overlying a top end of said sample container when said retaining arm is in said second position.

68. The apparatus of claim 64, wherein said transferring device comprises a substantially horizontal track extending from said supply magazine to said electrophoresis device and a robotic arm movable along said track to a first position for removing a sample from a preselected sample container to a second position for dispensing said sample to said gel tube, and wherein movement of said robotic arm toward said supply magazine moves said retaining arm to said second position.

69. The apparatus of claim 68, wherein said retaining arm is pivotally mounted and said first position of said retaining arm is in a path of said robotic arm whereby said robotic arm contacts said retaining arm when moved toward said supply magazine and pivots said retaining arm to said second position.

70. The apparatus of claim 62, wherein said transferring device comprises a robotic arm operatively connected to said microprocessor.

71. The apparatus of claim 62, wherein said microprocessor controls said robotic arm to sequentially remove a sample from said sample containers and dispense said sample sequentially to a first end of a respective gel tube.

72. The apparatus of claim 62, wherein each of said gel tubes have a first open end and second open end, said rack including a chamber for containing a first buffer solution and being in communication with said first end of said tubes, said tank being dimensioned for containing a second buffer solution in contact with said second end of said tubes, and an electrical power source having a first electrode in said chamber for contacting said first solution and a second electrode in said tank for contacting said second solution.

73. The apparatus of claim 62, further comprising an electrical power source for applying an electrical potential between first and second ends of said gel tubes, wherein said microprocessor is operatively connected to said power source, and wherein said microprocessor measures a voltage and current applied over time between said first and second ends of said gel tubes.

74. The apparatus of claim 62, wherein said microprocessor plots said measured voltage and current as a function of time.

75. The apparatus of claim 62, wherein said gel tube contains an IPG gel.

76. The apparatus of claim 62, further comprising a temperature control device for controlling a temperature of said tank, wherein said temperature control device is operatively connected to and operated by said microprocessor.

* * * * *

UNITED STATES PATENT AND TRADEMARK OFFICE
CERTIFICATE OF CORRECTION

PATENT NO. : 6,537,434 B1
DATED : March 25, 2003
INVENTOR(S) : McGrath et al.

It is certified that error appears in the above-identified patent and that said Letters Patent is hereby corrected as shown below:

Column 1,
Line 11, the following information should be inserted:
-- This invention was made with United States Government support under cooperative agreement number 70NANB5H1075 awarded by the National Institute of Standards and Technology. The government has certain rights in the invention. --.

Signed and Sealed this

Fifteenth Day of November, 2005

JON W. DUDAS
*Director of the United States Patent and Trademark Office*